(12) United States Patent
Bonn

(10) Patent No.: US 8,069,553 B2
(45) Date of Patent: Dec. 6, 2011

(54) METHOD FOR CONSTRUCTING A DIPOLE ANTENNA

(75) Inventor: Kenlyn S. Bonn, Boulder, CO (US)

(73) Assignee: Vivant Medical, Inc., Boulder, CO (US)

( * ) Notice: Subject to any disclaimer, the term of this patent is extended or adjusted under 35 U.S.C. 154(b) by 78 days.

(21) Appl. No.: 12/556,238

(22) Filed: Sep. 9, 2009

(65) Prior Publication Data

US 2011/0056069 A1  Mar. 10, 2011

(51) Int. Cl.
*H01P 11/00* (2006.01)

(52) U.S. Cl. .................. 29/600; 29/592.1; 343/700 MS

(58) Field of Classification Search .............. 29/600, 29/592.1; 264/272.11–272.15, 272.17, 272.19; 343/700 MS, 895
See application file for complete search history.

(56) References Cited

U.S. PATENT DOCUMENTS

| | | | |
|---|---|---|---|
| 4,725,395 A * | 2/1988 | Gasparaitis et al. .......... | 264/250 |
| 4,841,988 A | 6/1989 | Fetter et al. | |
| 5,358,515 A | 10/1994 | Hürter et al. | |
| 5,836,072 A * | 11/1998 | Sullivan et al. ............... | 29/600 |
| 5,916,240 A | 6/1999 | Rudie et al. | |
| 6,878,147 B2 * | 4/2005 | Prakash et al. ............... | 606/33 |
| 7,147,632 B2 * | 12/2006 | Prakash et al. ............... | 606/33 |
| 7,594,313 B2 * | 9/2009 | Prakash et al. ............... | 29/600 |
| 2007/0233057 A1 | 10/2007 | Konishi | |
| 2009/0187180 A1 | 7/2009 | Brannan | |
| 2009/0295674 A1 | 12/2009 | Bonn | |
| 2010/0045558 A1 | 2/2010 | Rossetto | |
| 2010/0045559 A1 | 2/2010 | Rossetto | |

FOREIGN PATENT DOCUMENTS

| | | |
|---|---|---|
| DE | 390937 | 3/1924 |
| DE | 1099658 | 2/1961 |
| DE | 1139927 | 11/1962 |
| DE | 1149832 | 6/1963 |
| DE | 1439302 | 1/1969 |
| DE | 2439587 | 2/1975 |
| DE | 2455174 | 5/1975 |
| DE | 2407559 | 8/1975 |
| DE | 2415263 | 10/1975 |
| DE | 2429021 | 1/1976 |
| DE | 2460481 | 6/1976 |
| DE | 2602517 | 7/1976 |
| DE | 2504280 | 8/1976 |
| DE | 2627679 | 1/1977 |
| DE | 2540968 | 3/1977 |
| DE | 2820908 | 11/1978 |
| DE | 2803275 | 8/1979 |

(Continued)

OTHER PUBLICATIONS

U.S. Appl. No. 12/535,851, filed Aug. 5, 2009.

(Continued)

*Primary Examiner* — Minh Trinh

(57) ABSTRACT

A method of fabricating a microwave antenna assembly is disclosed. The fabrication method includes providing a proximal portion having an inner conductor and an outer conductor, the inner conductor extending at least partially therein. The method further includes providing a distal portion disposed distally of the proximal portion, with the inner conductor extending at least partially therein. A high strength material may be injected from an inflow slot to an outflow slot of the distal portion such that the material is disposed in-between the inner conductor and a ceramic layer. The material bonds the distal portion and the ceramic layer to the proximal portion while providing mechanical strength to the distal portion.

17 Claims, 6 Drawing Sheets

FOREIGN PATENT DOCUMENTS

| | | |
|---|---|---|
| DE | 2823291 | 11/1979 |
| DE | 2946728 | 5/1981 |
| DE | 3143421 | 5/1982 |
| DE | 3045996 | 7/1982 |
| DE | 3120102 | 12/1982 |
| DE | 3510586 | 10/1986 |
| DE | 3604823 | 8/1987 |
| DE | 8712328 | 3/1988 |
| DE | 3711511 | 6/1988 |
| DE | 3904558 | 8/1990 |
| DE | 3942998 | 7/1991 |
| DE | 4238263 | 5/1993 |
| DE | 4303882 | 8/1994 |
| DE | 4339049 | 5/1995 |
| DE | 29616210 | 1/1997 |
| DE | 19608716 | 4/1997 |
| DE | 19751106 | 5/1998 |
| DE | 19717411 | 11/1998 |
| DE | 19751108 | 5/1999 |
| DE | 19801173 | 7/1999 |
| DE | 19848540 | 5/2000 |
| DE | 10224154 | 12/2003 |
| DE | 10328514 | 3/2005 |
| DE | 102004022206 | 12/2005 |
| DE | 202005015147 | 3/2006 |
| EP | 0 246 350 | 11/1987 |
| EP | 0 521 264 | 1/1993 |
| EP | 0 556 705 | 8/1993 |
| EP | 0 558 429 | 9/1993 |
| EP | 0 836 868 | 4/1998 |
| EP | 1 159 926 | 5/2001 |
| EP | 2128929 | 12/2009 |
| FR | 179 607 | 11/1906 |
| FR | 1 275 415 | 9/1960 |
| FR | 1 347 865 | 11/1963 |
| FR | 2 276 027 | 6/1974 |
| FR | 2 235 669 | 1/1975 |
| FR | 2 313 708 | 12/1976 |
| FR | 2 502 935 | 10/1982 |
| FR | 2 517 953 | 6/1983 |
| FR | 2 573 301 | 11/1984 |
| FR | 2 862 813 | 5/2005 |
| FR | 2 864 439 | 7/2005 |
| JP | 5-5106 | 1/1993 |
| JP | 05-40112 | 2/1993 |
| JP | 06343644 | 12/1994 |
| JP | 07265328 | 10/1995 |
| JP | 08056955 | 3/1996 |
| JP | 08252263 | 10/1996 |
| JP | 09010223 | 1/1997 |
| JP | 11244298 | 9/1999 |
| JP | 2000342599 | 12/2000 |
| JP | 2000350732 | 12/2000 |
| JP | 2001008944 | 1/2001 |
| JP | 2001029356 | 2/2001 |
| JP | 2001128990 | 5/2001 |
| SU | 166452 | 11/1964 |
| SU | 401367 | 11/1974 |
| SU | 727201 | 4/1980 |

OTHER PUBLICATIONS

Alexander et al., "Magnetic Resonance Image-Directed Stereotactic Neurosurgery: Use of Image Fusion with Computerized Tomography to Enhance Spatial Accuracy" Journal Neurosurgery, 83 (1995), pp. 271-276.
Anderson et al., "A Numerical Study of Rapid Heating for High Temperature Radio Frequency Hyperthermia" International Journal of Bio-Medical Computing, 35 (1994), pp. 297-307.
Anonymous. (1999) Auto Suture MIBB Site Marker: Single Use Clip Applier, United States Surgical (Product instructions), 2 pages.
Anonymous. (2001) Disposable Chiba Biopsy Needles and Trays, Biopsy and Special Purpose Needles Cook Diagnostic and Interventional Products Catalog (products list), 4 pages.
Anonymous. (1987) Homer Mammalok™ Breast Lesion Needle/Wire Localizer, Namic ® Angiographic Systems Division, Glens Falls, New York, (Hospital products price list), 4 pages.
Anonymous. (1999) MIBB Site Marker, United States Surgical (Sales brochure), 4 pages.
Anonymous. Blunt Tubes with Finished Ends. Pointed Cannula, Popper & Sons Biomedical Instrument Division, (Products Price List), one page, Jul. 19, 2000.
Anonymous. Ground Cannulae, ISPG, New Milford, CT, (Advertisement) one page, Jul. 19, 2000.
B. Levy M.D. et al., "Randomized Trial of Suture Versus Electrosurgical Bipolar Vessel Sealing in Vaginal Hysterectomy" Obstetrics & Gynecology, vol. 102, No. 1, Jul. 2003.
B. Levy M.D. et al., "Update on Hysterectomy New Technologies and Techniques" OBG Management, Feb. 2003.
B. Levy M.D., "Use of a New Vessel Ligation Device During Vaginal Hysterectomy" FIGO 2000, Washington, D.C.
B. F. Mullan et al., (May 1999) "Lung Nodules: Improved Wire for CT-Guided Localization," Radiology 211:561-565.
B. T. Heniford M.D. et al., "Initial Research and Clinical Results with an Electrothermal Bipolar Vessel Sealer" Oct. 1999.
Bergdahl et al., "Studies on Coagulation and the Development of an Automatic Computerized Bipolar Coagulator" Journal of Neurosurgery 75:1 (Jul. 1991), pp. 148-151.
Bulletin of the American Physical Society, vol. 47, No. 5, Aug. 2002, p. 41.
C. F. Gottlieb et al., "Interstitial Microwave Hyperthermia Applicators having Submillimetre Diameters", Int. J. Hyperthermia, vol. 6, No. 3, pp. 707-714, 1990.
C. H. Dumey et al., "Antennas for Medical Applications", Antenna Handbook: Theory Application and Design, p. 24-40, Van Nostrand Reinhold, 1988 New York, V.T. Lo, S.W. Lee.
Carbonell et al., "Comparison of the Gyrus PlasmaKinetic Sealer and the Valleylab LigaSure™ Device in the Hemostasis of Small, Medium, and Large-Sized Arteries" Carolinas Laparoscopic and Advanced Surgery Program, Carolinas Medical Center, Charlotte, NC 2003.
Carus et al., "Initial Experience With the LigaSure™ Vessel Sealing System in Abdominal Surgery" Innovations That Work, Jun. 2002.
Chicharo et al., "A Sliding Goertzel Algorithm" Aug. 1996 DOS pp. 283-297 Signal Processing, Elsevier Science Publishers B.V. Amsterdam, NL, vol. 52, No. 3.
Chou, C.K., (1995) "Radiofrequency Hyperthermia in Cancer Therapy," Chapter 941n Biologic Effects of Nonionizing Electromagnetic Fields, CRC Press, Inc., pp. 1424-1428.
Chung et al., "Clinical Experience of Sutureless Closed Hemorrhoidectomy with LigaSure™" Diseases of the Colon & Rectum, vol. 46, No. 1, Jan. 2003.
Cosman et al., "Methods of Making Nervous System Lesions" In William RH, Rengachary SS (eds): Neurosurgery, New York: McGraw-Hill, vol. 111, (1984), pp. 2490-2499.
Cosman et al., "Radiofrequency Lesion Generation and its Effect on Tissue Impedance", Applied Neurophysiology, 51:230-242, 1988.
Cosman et al., "Theoretical Aspects of Radiofrequency Lesions in the Dorsal Root Entry Zone" Neurosurgery 15:(1984), pp. 945-950.
Crawford et al., "Use of the LigaSure™ Vessel Sealing System in Urologic Cancer Surger" Grand Rounds In Urology 1999, vol. 1, Issue 4, pp. 10-17.
Dulemba et al., "Use of a Bipolar Electrothermal Vessel Sealer in Laparoscopically Assisted Vaginal Hysterectomy" Sales/Product Literature; Jan. 2004.
E. David Crawford, "Evaluation of a New Vessel Sealing Device in Urologic Cancer Surgery" Sales/Product Literature 2000.
E. David Crawford, "Use of a Novel Vessel Sealing Technology in Management of the Dorsal Veinous Complex" Sales/Product Literature 2000.
Esterline, "Light Key Projection Keyboard" 2004 Advanced Input Systems, located at: <http://www.advanced-input.com/lightkey> last visited on Feb. 10, 2005.
Esterline Product Literature, "Light Key: Visualize a Virtual Keyboard. One With No Moving Parts", Nov. 1, 2003; 4 pages.
Geddes et al., "The Measurement of Physiologic Events by Electrical Impedence" Am. J. MI, Jan. Mar. 1964, pp. 16-27.
Goldberg et al., "Image-guided Radiofrequency Tumor Ablation: Challenges and Opportunities—Part I", (2001) J Vasc. Interv. Radiol, vol. 12, pp. 1021-1032.

Goldberg et al., "Tissue Ablation with Radiofrequency: Effect of Probe Size, Gauge, Duration, and Temperature on Lesion Volume" Acad Radio (1995) vol. 2, No. 5, pp. 399-404.

H. Schwarzmaier et al., "Magnetic Resonance Imaging of Microwave Induced Tissue Heating" Dept. of Laser Medicine & Dept. of Diagnostic Radiology; Heinrich-Heine-University, Duesseldorf, Germany; Dec. 8, 1994; pp. 729-731.

Heniford et al., "Initial Results with an Electrothermal Bipolar Vessel Sealer" Surgical Endoscopy (2001) 15:799-801.

Herman at al., "Laparoscopic Intestinal Resection With the LigaSure™ Vessel Sealing System: A Case Report" Innovations That Work, Feb. 2002.

Humphries Jr. et al., "Finite Element Codes to Model Electrical Heating and Non LInear Thermal Transport in Biological Media", Proc. ASME HTD-355, 131 (1997).

Ian D. McRury et al., The Effect of Ablation Sequence and Duration on Lesion Shape Using Rapidly Pulsed Radiofrequency Energy Through Electrodes, Feb. 2000, Springer Netherlands, vol. 4; No. 1, pp. 307-320.

Jarrett et al., "Use of the LigaSure™ Vessel Sealing System for Peri-Hilar Vessels in Laparoscopic Nephrectomy" Sales/Product Literature 2000.

Johnson et al., "Evaluation of a Bipolar Electrothermal Vessel Sealing Device in Hemorrhoidectomy" Sales/Product Literature, Jan. 2004.

Johnson, "Evaluation of the LigaSure™ Vessel Sealing System in Hemorrhoidectormy" American College Of Surgeons (ACS) Clinic La Congress Poster (2000).

Johnson, "Use of the LigaSure™ Vessel Sealing System in Bloodless Hemorrhoidectomy" Innovations That Work, Mar. 2000.

Joseph G. Andriole M.D. et al., "Biopsy Needle Characteristics Assessed in the Laboratory", Radiology 148: 659-662, Sep. 1983.

Joseph Ortenberg, "LigaSure™ System Used in Laparoscopic 1st and 2nd Stage Orchiopexy" Innovations That Work, Nov. 2002.

K. Ogata, Modern Control Engineering, Prentice-Hall, Englewood Cliffs, N.J., 1970.

Kennedy et al., "High-burst-strength, feedback-controlled bipolar vessel sealing" Surgical Endoscopy (1998) 12: 876-878.

Kopans, D.B. et al., (Nov. 1985) "Spring Hookwire Breast Lesion Localizer: Use with Rigid-Compression. Mammographic Systems," Radiology 157(2):537-538.

Koyle et al., "Laparoscopic Palomo Varicocele Ligation in Children and Adolescents" Pediatric Endosurgery & Innovative Techniques, vol. 6, No. 1, 2002.

LigaSure™ Vessel Sealing System, the Seal of Confidence in General , Gynecologic, Urologic, and Laparaoscopic Surgery, Sales/Product Literature, Jan. 2004.

Livraghi et al., (1995) "Saline-enhanced RF Tissue Ablation in the Treatment of Liver Metastases", Radiology, pp. 205-210.

Lyndon B. Johnson Space Center, Houston, Texas, "Compact Directional Microwave Antenna for Localized Heating," NASA Tech Briefs, Mar. 2008.

M. A. Astrahan, "A Localized Current Field Hyperthermia System for Use with 192-Iridium Interstitial Implants" Medical Physics. 9(3), May/Jun. 1982.

Magdy F. Iskander et al., "Design Optimization of Interstitial Antennas", IEEE Transactions on Biomedical Engineering, vol. 36, No. 2, Feb. 1989, pp. 238-246.

McGahan et al., (1995) "Percutaneous Ultrasound-guided Radiofrequency Electrocautery Ablation of Prostate Tissue in Dogs", Acad Radiol, vol. 2, No. 1: pp. 61-65.

McLellan et al., "Vessel Sealing for Hemostasis During Pelvic Surgery" Intl Federation of Gynecology and Obstetrics FIGO World Congress 2000, Washington, DC.

MDTECH product literature (Dec. 1999) "FlexStrand": product description, 1 page.

MDTECH product literature (Mar. 2000) I'D Wire: product description, 1 page.

Medtrex Brochure "The O.R. Pro 300" 1 page, Sep. 1998.

Michael Choti, "Abdominoperineal Resection with the LigaSure™ Vessel Sealing System and LigaSure™ Atlas 20 cm Open Instrument" Innovations That Work, Jun. 2003.

Muller et al., "Extended Left Hemicolectomy Using the LigaSure™ Vessel Sealing System" Innovations That Work. LJ, Sep. 1999.

Murakami, R. et al., (1995). "Treatment of Hepatocellular Carcinoma: Value of Percutaneous Microwave Coagulation," American Journal of Radiology (AJR) 164:1159-1164.

Ni Wei et al., "A Signal Processing Method for the Coriolis Mass Flowmeter Based on a Normalized . . . " Journal of Applied Sciences Yingyong Kexue Xuebao, Shangha CN, vol. 23, No. 2:(Mar. 2005); pp. 160-184.

Ogden, "Goertzel Alternative to the Fourier Transform" Jun. 1993 pp. 485-487 Electronics World; Reed Business Publishing, Sutton, Surrey, BG, vol. 99, No. 9, 1687.

Olsson M.D. et al., "Radical Cystectomy in Females" Current Surgical Techniques in Urology, vol. 14, Issue 3, 2001.

Organ, L W., "Electrophysiologic Principles of Radiofrequency Lesion Making" Appl. Neurophysiol, vol. 39: pp. 69-76 (1976/1977).

P.R. Stauffer et al., "Interstitial Heating Technologies", Thermoradiotheray and Thermochemotherapy (1995) vol. I, Biology, Physiology, Physics, pp. 279-320.

Palazzo et al., "Randomized clinical trial of LigaSure™ versus open haemorrhoidectomy" British Journal of Surgery 2002,89,154-157 "Innovations in Electrosurgery" Sales/Product Literature; Dec. 31, 2000.

Paul G. Horgan, "A Novel Technique for Parenchymal Division During Hepatectomy" The American Journal of Surgery, vol. 181, No. 3, Apr. 2001, pp. 236-237.

Peterson et al., "Comparison of Healing Process Following Ligation with Sutures and Bipolar Vessel Sealing" Surgical Technology International (2001).

R. Gennari et al., (Jun. 2000) "Use of Technetium-99m-Labeled Colloid Albumin for Preoperative and Intraoperative Localization of Non palpable Breast Lesions," American College of Surgeons. 190(6):692-699.

Valleylab Brochure, "Reducing Needlestick Injuries in the Operating Room" 1 page, Mar. 2001.

Reidenbach, (1995) "First Experimental Results with Special Applicators for High-Frequency Interstitial Thermotherapy", Society Minimally Invasive Therapy, 4(Suppl 1):40 (Abstr).

Richard Wolf Medical Instruments Corp. Brochure, "Kleppinger Bipolar Forceps & Bipolar Generator" 3 pages, Jan. 1989.

Rothenberg et al., "Use of the LigaSure™ Vessel Sealing System in Minimally Invasive Surgery in Children" Intl Pediatric Endosurgery Group (I PEG) 2000.

Sayfan et al., "Sutureless Closed Hemorrhoidectomy: A New Technique" Annals of Surgery, vol. 234, No. 1, Jul. 2001, pp. 21-24.

Sengupta et al., "Use of a Computer-Controlled Bipolar Diathermy System in Radical Prostatectomies and Other Open Urological Surgery" ANZ Journal of Surgery (2001) 71.9 pp. 538-540.

Sigel et al., "The Mechanism of Blood Vessel Closure by High Frequency Electrocoagulation" Surgery Gynecology & Obstetrics, Oct. 1965 pp. 823-831.

Solbiati et al., (2001) "Percutaneous Radio-frequency Ablation of Hepatic Metastases from Colorectal Cancer: Long-term Results in 117 Patients", Radiology, vol. 221, pp. 159-166.

Strasberg et al., "Use of a Bipolar Vassel-Sealing Device for Parenchymal Transection During Liver Surgery" Journal of Gastrointestinal Surgery, vol. 6, No. 4, Jul./Aug. 2002 pp. 569-574.

Stuart W. Young, Nuclear Magnetic Resonance Imaging—Basic Principles, Raven Press, New York, 1984.

Sugita et al., "Bipolar Coagulator with Automatic Thermocontrol" J. Neurosurg., vol. 41, Dec. 1944, pp. 777-779.

Sylvain Labonte et al., "Monopole Antennas for Microwave Catheter Ablation", IEEE Trans. on Microwave Theory and Techniques, vol. 44, No. 10, pp. 1832-1840, Oct. 1995.

T. Matsukawa et al., "Percutaneous Microwave Coagulation Therapy in Liver Tumors", Acta Radiologica, vol. 38, pp. 410-415, 1997.

T. Seki et al., (1994) "Ultrasonically Guided Percutaneous Microwave Coagulation Therapy for Small Hepatocellular Carcinoma," Cancer 74(3):817-825.

Urologix, Inc.-Medical Professionals: Targis™ Technology (Date Unknown). "Overcoming the Challenge" located at: <http://www.urologix.com!medicaUtechnology.html > last visited on Apr. 27, 2001, 3 pages.

Urrutia et al., (1988). "Retractable-Barb Needle for Breast Lesion Localization: Use in 60 Cases," Radiology 169(3):845-847.
Valleylab Brochure, "Valleylab Electroshield Monitoring System" 2 pages, Nov. 1995.
ValleyLab Brochure, "Electosurgery: A Historical Overview", Innovations in Electrosurgery, 1999.
Vallfors et al., "Automatically Controlled Bipolar Electrocoagulation-'COA-COMP'" Neurosurgical Review 7:2-3 (1984) pp. 187-190.
W. Scott Helton, "LigaSure™ Vessel Sealing System: Revolutionary Hemostasis Product for General Surgery" Sales/Product Literature 1999.
Wald et al., "Accidental Burns", JAMA, Aug. 16, 1971, vol. 217, No. 7, pp. 916-921.
Walt Boyles, "Instrumentation Reference Book", 2002, Butterworth-Heinemann, pp. 262-264.
European Search Report EP 98300964.8 dated Dec. 13, 2000.
European Search Report EP 98944778 dated Nov. 7, 2000.
European Search Report EP 98958575.7 dated Oct. 29, 2002.
European Search Report EP 03721482 dated Feb. 6, 2006.
European Search Report EP 04009964 dated Jul. 28, 2004.
European Search Report EP 04013772 dated Apr. 11, 2005.
European Search Report EP 04015980 dated Nov. 3, 2004.
European Search Report EP 04015981.6 dated Oct. 25, 2004.
European Search Report EP 04027314 dated Mar. 31, 2005.
European Search Report EP 04027479 dated Mar. 17, 2005.
European Search Report EP 04027705 dated Feb. 10, 2005.
European Search Report EP 04710258 dated Oct. 15, 2004.
European Search Report EP 04752343.6 dated Jul. 31, 2007.
European Search Report EP 04778192.7 dated Jul. 1, 2009.
European Search Report EP 05002027.0 dated May 12, 2005.
European Search Report EP 05002769.7 dated Jun. 19, 2006.
European Search Report EP 05013463.4 dated Oct. 7, 2005.
European Search Report EP 05013895 dated Oct. 21, 2005.
European Search Report EP 05014156.3 dated Jan. 4, 2006.
European Search Report EP 05016399 dated Jan. 13, 2006.
European Search Report EP 05017281 dated Nov. 24, 2005.
European Search Report EP 05019130.3 dated Oct. 27, 2005.
European Search Report EP 05019882 dated Feb. 16, 2006.
European Search Report EP 05020665.5 dated Feb. 27, 2006.
European Search Report EP 05020666.3 dated Feb. 27, 2006.
European Search Report EP 05021025.1 dated Mar. 13, 2006.
European Search Report EP 05021197.8 dated Feb. 20, 2006.
European Search Report EP 05021777 dated Feb. 23, 2006.
European Search Report EP 05021779.3 dated Feb. 2, 2006.
European Search Report EP 05021780.1 dated Feb. 23, 2006.
European Search Report EP 05021935 dated Jan. 27, 2006.
European Search Report EP 05021936.9 dated Feb. 6, 2006.
European Search Report EP 05021937.7 dated Jan. 23, 2006.
European Search Report EP 05021939 dated Jan. 27, 2006.
European Search Report EP 05021944.3 dated Jan. 25, 2006.
European Search Report EP 05022350.2 dated Jan. 30, 2006.
European Search Report EP 05023017.6 dated Feb. 24, 2006.
European Search Report EP 05025423.4 dated Jan. 19, 2007.
European Search Report EP 05025424 dated Jan. 30, 2007.
European Search Report EP 05810523 dated Jan. 29, 2009.
European Search Report EP 06000708.5 dated May 15, 2006.
European Search Report EP 06002279.5 dated Mar. 30, 2006.
European Search Report EP 06005185.1 dated May 10, 2006.
European Search Report EP 06005540 dated Sep. 24, 2007.
European Search Report EP 06006717.0 dated Aug. 11, 2006.
European Search Report EP 06006961 dated Oct. 22, 2007.
European Search Report EP 06006963 dated Jul. 25, 2006.
European Search Report EP 06008779.8 dated Jul. 13, 2006.
European Search Report EP 06009435 dated Jul. 13, 2006.
European Search Report EP 06010499.9 dated Jan. 29, 2008.
European Search Report EP 06014461.5 dated Oct. 31, 2006.
European Search Report EP 06018206.0 dated Oct. 20, 2006.
European Search Report EP 06019768 dated Jan. 17, 2007.
European Search Report EP 06020574.7 dated Oct. 2, 2007.
European Search Report EP 06020583.8 dated Feb. 7, 2007.
European Search Report EP 06020584.6 dated Feb. 1, 2007.
European Search Report EP 06020756.0 dated Feb. 16, 2007.
European Search Report EP 06022028.2 dated Feb. 13, 2007.
European Search Report EP 06023756.7 dated Feb. 21, 2008.
European Search Report EP 06024122.1 dated Apr. 16, 2007.
European Search Report EP 06024123.9 dated Mar. 6, 2007.
European Search Report EP 06025700.3 dated Apr. 12, 2007.
European Search Report EP 07000885.9 dated May 15, 2007.
European Search Report EP 07001480.8 dated Apr. 19, 2007.
European Search Report EP 07001481.6 dated May 2, 2007.
European Search Report EP 07001485.7 dated May 23, 2007.
European Search Report EP 07001488.1 dated Jun. 5, 2007.
European Search Report EP 07001489.9 dated Dec. 20, 2007.
European Search Report EP 07001491 dated Jun. 6, 2007.
European Search Report EP 07001527.6 dated May 18, 2007.
European Search Report EP 07007783.9 dated Aug. 14, 2007.
European Search Report EP 07008207.8 dated Sep. 13, 2007.
European Search Report EP 07009026.1 dated Oct. 8, 2007.
European Search Report EP 07009028 dated Jul. 16, 2007.
European Search Report EP 07009029.5 dated Jul. 20, 2007.
European Search Report EP 07009321.6 dated Aug. 28, 2007.
European Search Report EP 07009322.4 dated Jan. 14, 2008.
European Search Report EP 07010672.9 dated Oct. 16, 2007.
European Search Report EP 07010673.7 dated Oct. 5, 2007.
European Search Report EP 07013779.9 dated Oct. 26, 2007.
European Search Report EP 07015191.5 dated Jan. 23, 2007.
European Search Report EP 07015601.3 dated Jan. 4, 2007.
European Search Report EP 07015602.1 dated Dec. 20, 2007.
European Search Report EP 07018375.1 dated Jan. 8, 2008.
European Search Report EP 07018821 dated Jan. 14, 2008.
European Search Report EP 07019173.9 dated Feb. 12, 2008.
European Search Report EP 07019174.7 dated Jan. 29, 2008.
European Search Report EP 07019178.8 dated Feb. 12, 2008.
European Search Report EP 07020283.3 dated Feb. 5, 2008.
European Search Report EP 07253835.8 dated Dec. 20, 2007.
European Search Report EP 08001019 dated Sep. 23, 2008.
European Search Report EP 08004975 dated Jul. 24, 2008.
European Search Report EP 08006731.7 dated Jul. 29, 2008.
European Search Report EP 08006733 dated Jul. 7, 2008.
European Search Report EP 08006734.1 dated Aug. 18, 2008.
European Search Report EP 08006735.8 dated Jan. 8, 2009.
European Search Report EP 08011282 dated Aug. 14, 2009.
European Search Report EP 08011705 dated Aug. 20, 2009.
European Search Report EP 08012829.1 dated Oct. 29, 2008.
European Search Report EP 08015842 dated Dec. 5, 2008.
European Search Report EP 08019920.1 dated Mar. 27, 2009.
European Search Report EP 08169973.8 dated Apr. 6, 2009.
European Search Report EP 09156861.8 dated Aug. 4, 2009.
European Search Report EP 09161502.1 dated Sep. 2, 2009.
European Search Report EP 09166708 dated Oct. 15, 2009.
International Search Report PCT/US98/18640 dated Jan. 29, 1998.
International Search Report PCT/US98/23950 dated Jan. 14, 1998.
International Search Report PCT/US99/24869 dated Feb. 11, 2000.
International Search Report PCT/US01/11218 dated Aug. 14, 2001.
International Search Report PCT/US01/11224 dated Nov. 13, 2001.
International Search Report PCT/US01/11340 dated Aug. 16, 2001.
International Search Report PCT/US01/11420 dated Oct. 16, 2001.
International Search Report PCT/US02/01890 dated Jul. 25, 2002.
International Search Report PCT/US02/11100 dated Jul. 16, 2002.
International Search Report PCT/US03/09483 dated Aug. 13, 2003.
International Search Report PCT/US03/22900 dated Dec. 2, 2003.
International Search Report PCT/US03/37110 dated Jul. 25, 2005.
International Search Report PCT/US03/37111 dated Jul. 28, 2004.
International Search Report PCT/US03/37310 dated Aug. 13, 2004.
International Search Report PCT/US04/04685 dated Aug. 27, 2004.
International Search Report PCT/US04/13273 dated Dec. 15, 2004.
International Search Report PCT/US04/15311 dated Jan. 12, 2004.
International Search Report PCT/US05/36168 dated Aug. 28, 2006.
International Search Report PCT/US08/052460 dated Apr. 24, 2008.
International Search Report PCT/US09/31658 dated Mar. 11, 2009.

* cited by examiner

METHOD FOR CONSTRUCTING A DIPOLE ANTENNA

BACKGROUND

1. Technical Field

The present disclosure relates generally to microwave applicators used in tissue ablation procedures. More particularly, the present disclosure is directed to a microwave applicator having either a liquid or solid loaded tip dipole antenna.

2. Background of Related Art

Treatment of certain diseases requires destruction of malignant tissue growths (e.g., tumors). It is known that tumor cells denature at elevated temperatures that are slightly lower than temperatures injurious to surrounding healthy cells. Therefore, known treatment methods, such as hyperthermia therapy, heat tumor cells to temperatures above 41° C., while maintaining adjacent healthy cells at lower temperatures to avoid irreversible cell damage. Such methods involve applying electromagnetic radiation to heat tissue and include ablation and coagulation of tissue. In particular, microwave energy is used to coagulate and/or ablate tissue to denature or kill the cancerous cells.

Microwave energy is applied via microwave ablation antennas that penetrate tissue to reach tumors. There are several types of microwave antennas, such as monopole and dipole. In monopole and dipole antennas, microwave energy radiates perpendicularly from the axis of the conductor. A monopole antenna includes a single, elongated microwave conductor. Dipole antennas may have a coaxial construction including an inner conductor and an outer conductor separated by a dielectric portion. More specifically, dipole microwave antennas may have a long, thin inner conductor that extends along a longitudinal axis of the antenna and is surrounded by an outer conductor. In certain variations, a portion or portions of the outer conductor may be selectively removed to provide for more effective outward radiation of energy. This type of microwave antenna construction is typically referred to as a "leaky waveguide" or "leaky coaxial" antenna.

Conventional microwave antennas typically has a long, thin inner conductor which extends along the axis of the probe and is surrounded by a dielectric material and is further surrounded by an outer conductor around the dielectric material such that the outer conductor also extends along the axis of the probe. In another variation of the probe which provides for effective outward radiation of energy or heating, a portion or portions of the outer conductor can be selectively removed. This type of construction is typically referred to as a "leaky waveguide" or "leaky coaxial" antenna. Another variation on the microwave probe involves having the tip formed in a uniform spiral pattern, such as a helix, to provide the necessary configuration for effective radiation. This variation can be used to direct energy in a particular direction, e.g., perpendicular to the axis, in a forward direction (i.e., towards the distal end of the antenna), or a combination thereof.

Invasive procedures and devices have been developed in which a microwave antenna probe may be either inserted directly into a point of treatment via a normal body orifice or percutaneously inserted. Such invasive procedures and devices potentially provide better temperature control of the tissue being treated. Because of the small difference between the temperature required for denaturing malignant cells and the temperature injurious to healthy cells, a known heating pattern and predictable temperature control is important so that heating is confined to the tissue to be treated. For instance, hyperthermia treatment at the threshold temperature of about 41.5° C. generally has little effect on most malignant growths of cells. However, at slightly elevated temperatures above the approximate range of 43° C. to 45° C., thermal damage to most types of normal cells is routinely observed; accordingly, great care must be taken not to exceed these temperatures in healthy tissue.

However, many types of malignancies are difficult to reach and treat using non-invasive techniques or by using invasive antenna probes designed to be inserted into a normal body orifice, i.e., a body opening which is easily accessible. These types of conventional probes may be more flexible and may also avoid the need to separately sterilize the probe; however, they are structurally weak and typically require the use of an introducer or catheter to gain access to within the body. Further, the manufacturing techniques for the conventional probe tend to be cumbersome, time consuming, and prohibitively expensive. Moreover, the addition of introducers and catheters necessarily increase the diameter of the incision or access opening into the body thereby making the use of such probes more invasive and further increasing the probability of any complications that may arise.

SUMMARY

A method of fabricating a microwave antenna assembly, which is structurally robust enough for unaided direct insertion into tissue is described herein. The microwave antenna assembly is generally comprised of a radiating portion which may be connected to a feedline (or shaft) which in turn may be connected by a cable to a power generating source such as a generator. The microwave assembly may be a monopole microwave antenna assembly but is preferably a dipole assembly. The distal portion of the radiating portion preferably has a tapered end which terminates at a tip to allow for the direct insertion into tissue with minimal resistance. The proximal portion is located proximally of the distal portion.

The adequate rigidity necessary for unaided direct insertion of the antenna assembly into tissue, e.g., percutaneously, preferably comes in part by a variety of different methods. A method of fabricating an antenna includes providing a proximal portion having an inner conductor and an outer conductor, the inner conductor extending at least partially therein. The method further includes providing a distal portion disposed distally of the proximal portion, with the inner conductor extending at least partially therein. A high strength polyimide material may be injected from an inflow slot to an outflow slot of the distal portion such that the polyimide material is disposed in-between the inner conductor and a ceramic layer. The polyimide material bonds the distal portion and the ceramic layer to the proximal portion while providing mechanical strength to the distal portion.

To further aid in strengthening the antenna assemblies the inner conductor may be affixed within the distal radiating portion in a variety of ways, for instance, welding, brazing, soldering, or through the use of adhesives. Forcing the inner conductor into a tensile condition helps to force the outer diameter of the antenna into a compressive state. This bi-directional stress state in turn aids in rigidizing the antenna assembly.

To enable a compressive state to exist near the outer diameter of the distal portion, a ceramic layer may be bonded to the polyimide material. Materials such as ceramic generally have mechanical properties where fracturing or cracking in the material is more likely to occur under tensile loading conditions. Accordingly, placing the distal portion under pre-stressed conditions, may aid in preventing mechanical failure of the distal portion if the antenna were to incur bending moments during insertion into tissue which could subject the distal portion under tensile loads. The ceramic layer and a coolant jacket also act as a dielectric buffer for aiding in keeping the efficiency of the antenna constant event though tissue is changing.

BRIEF DESCRIPTION OF THE DRAWINGS

The above and other aspects, features, and advantages of the present disclosure will become more apparent in light of the following detailed description when taken in conjunction with the accompanying drawings in which.

DETAILED DESCRIPTION

Particular embodiments of the present disclosure will be described herein below with reference to the accompanying drawings. In the following description, well-known functions or constructions are not described in detail to avoid obscuring the present disclosure in unnecessary detail.

Figure 1:
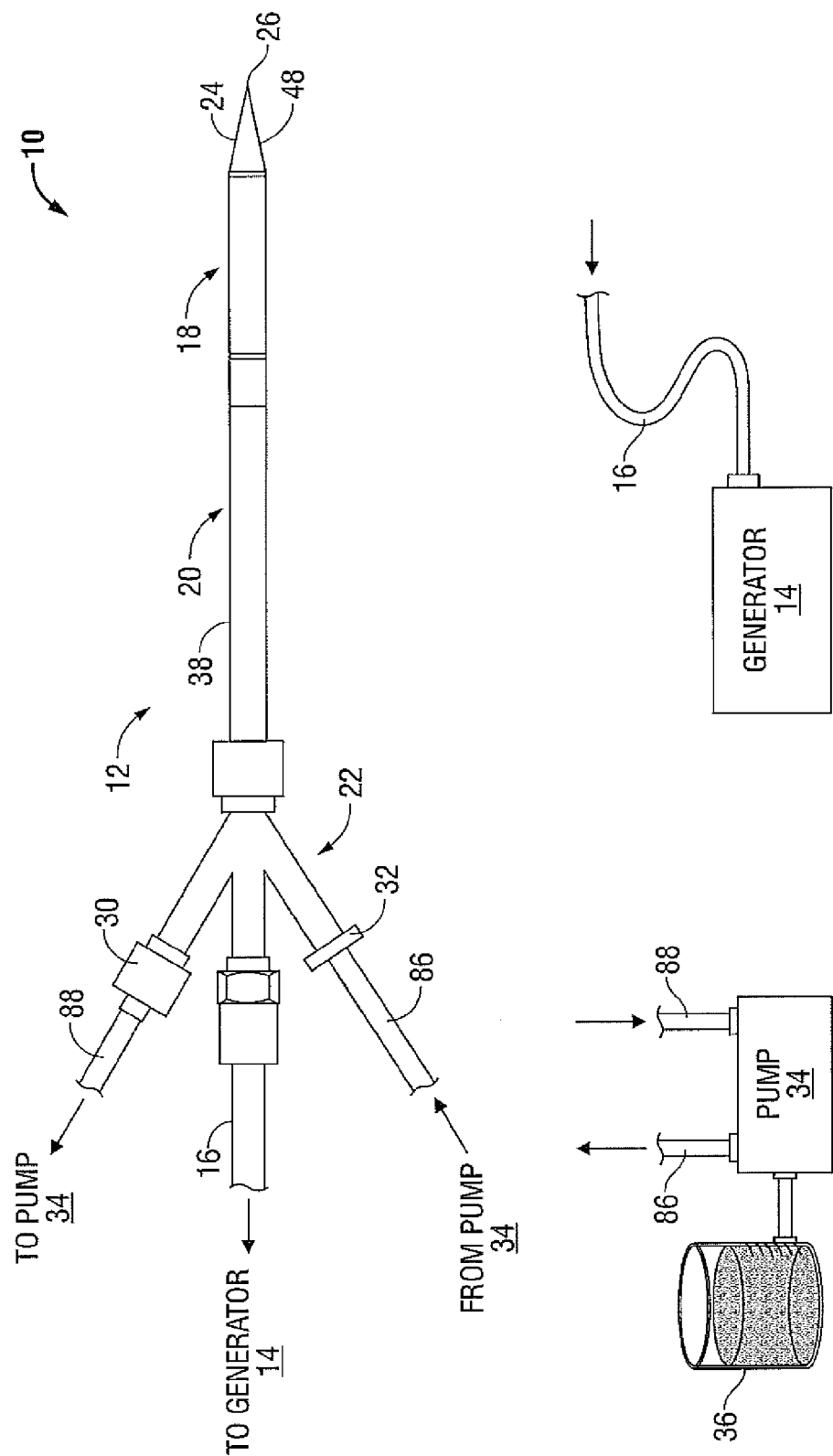
FIG. 1 is a schematic diagram of a microwave ablation system according to an embodiment of the present disclosure.

FIG. 1 shows a microwave ablation system 10 that includes a microwave antenna assembly 12 coupled to a microwave generator 14 via a flexible coaxial cable 16. The microwave antenna assembly 12 may be a dipole antenna of 1.6 cm in length. In order to ablate small tumors, microwave antenna assembly 12 has a Short Radiating Section (SRS). The microwave antenna assembly 12 is capable of reducing the antenna length to one-quarter of the wavelength length required, effectively using half the length of the half wave length dipole antenna. The generator 14 is configured to provide microwave energy at an operational frequency from about 500 MHz to about 5000 MHz.

Antenna assembly 12 is generally comprised of radiating portion 18, which may be connected by feedline 20 (or shaft) to the cable 16. More specifically, the antenna assembly 12 is coupled to the cable 16 through a connection hub 22. The connection hub 22 also includes an outlet fluid port 30 and an inlet fluid port 32 defined therein that are in fluid communication with a coolant jacket 38 and flow channel 13 (see FIG. 4). The coolant jacket 38 encloses a proximal portion 42 and the feedline 20 allowing coolant fluid from the ports 30 and 32 to be supplied and circulated around a portion of the antenna assembly 12. The ports 30 and 32 also include inner lumens defined therein (not shown) that are in fluid communication with the flow channel 13. The ports 30 and 32 are coupled to a supply pump 34 that is, in turn, coupled to a supply tank 36. The supply tank 36 stores the coolant fluid and maintains the fluid at a predetermined temperature. In one embodiment, the supply tank 36 may include a coolant unit which cools the returning liquid from the antenna assembly 12. In another embodiment, the coolant fluid may be a gas and/or a mixture of fluid and gas.

Assembly 12 also includes a tip 48 having a tapered end 24 that terminates, in one embodiment, at a pointed end 26 to allow for insertion into tissue with minimal resistance at a distal end of the radiating portion 18. In those cases where the radiating portion 18 is inserted into a pre-existing opening, tip 48 may be rounded or flat.

Figure 2:
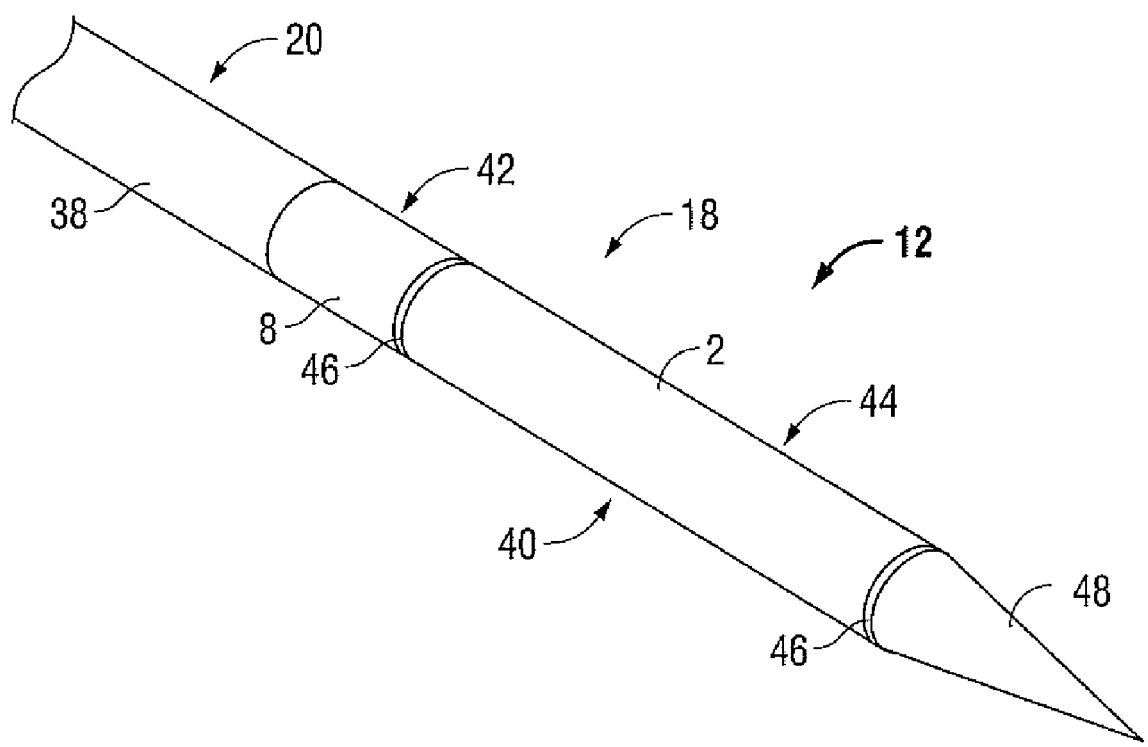
FIG. 2 is an isometric view of a microwave antenna assembly according to the present disclosure.
Figure 5:
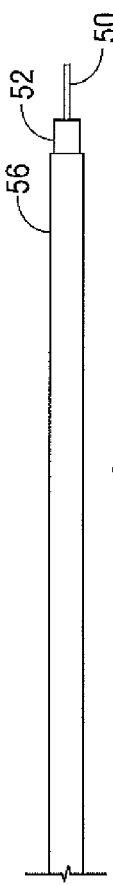
FIG. 5 is a side view of a distal portion of a feedline of the microwave antenna assembly of FIG. 2.

FIG. 2 illustrates the radiating portion 18 of the antenna assembly 12 having an unbalanced dipole antenna 40. The dipole antenna 40 includes a proximal portion 42 and a distal portion 44 interconnected by an injection molded seal 46. The distal portion 44 and the proximal portion 42 are of different, unequal lengths so that the dipole antenna 40 is unbalanced. In one embodiment, the distal portion 44 may be longer than the proximal portion 42. In one embodiment, in which the feedline 20 is formed from a coaxial cable, the outer conductor 56 and the inner insulator 52 may be sliced off to reveal the inner conductor 50, as shown in FIG. 5.

The dipole antenna 40 is coupled to the feedline 20 that electrically connects antenna assembly 12 to the generator 14 (FIG. 1). The assembly 12 includes a coolant jacket 38 coupled to a fluid seal 8 (see FIG. 4), which in turn is coupled to an injection molded seal 46. The coolant jacket 38 may be formed from a medical grade metal. The injection molded seal 46 may be made of a high strength polyimide resin. The polyimide resin may be VESPEL® sold by DuPont of Wilmington, Del.

Figure 3:
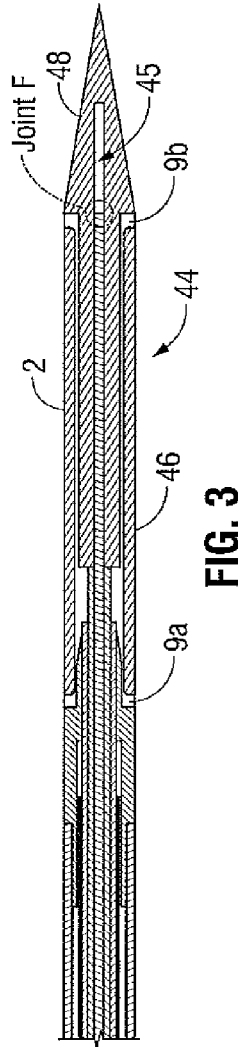
FIG. 3 is an enlarged, cross-sectional view of a portion of the microwave antenna assembly of FIG. 2.
Figure 4:
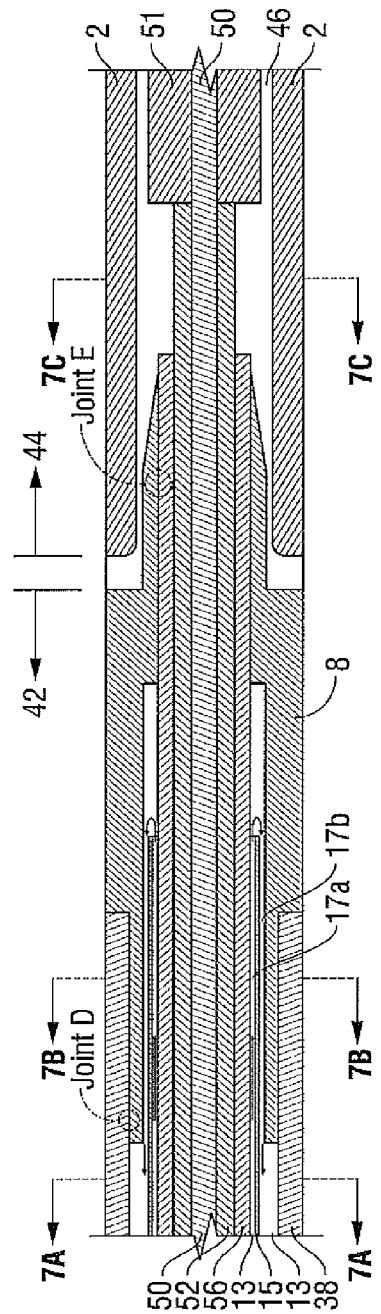
FIG. 4 is an enlarged, cross-sectional view of a portion of the microwave antenna assembly of FIG. 2.

In one embodiment, the injection molded seal 46 is fabricated by injecting a polyimide material into an inflow slot 9A to an outflow slot 9B of the distal portion 44. As shown in FIG. 3, the injection molded seal 46 is disposed in-between a distal radiating section 44 and the ceramic layer 2. The ceramic layer may be made of alumina ceramic. The injection molded seal 46 bonds the distal portion 44 and the ceramic layer 2 to the proximal portion 42 while providing mechanical strength to the distal portion 44. As shown in FIGS. 3-4, the feedline 20 includes an inner conductor 50 (e.g., wire) surrounded by an inner insulator 52, which is then surrounded by an outer conductor 56 (e.g., cylindrical conducting sheath). The inner and outer conductors 50, 56 may be constructed of copper, gold, stainless steel or other conductive metals with similar conductivity values. The metals may be plated with other materials, e.g., other conductive materials, to improve their properties, e.g., to improve conductivity or decrease energy loss, etc. In one embodiment, the inner insulator layer 52 is formed from a fluoropolymer, such as tetrafluorethylene, perfluorpropylene, and the like, and has a thickness of about 0.011-0.013 inches.

In one embodiment, the feedline 20 may be formed from a coaxial semi-rigid or flexible cable having a wire with a 0.047" outer diameter rated for 50 Ohms. The inner insulator 52 may have a dielectric constant from about 1 to 10.

Overlaying the outer conductor 56 is a flow channel 13 that cools the majority of the proximal portion 42. The flow channel 13 is in fluid communication with fluid ports 30, 32. A polyimide inflow sleeve 15 is disposed in the flow channel 13 to create an inflow channel 17a and an outflow channel 17b for the coolant. The abundance of cooling fluid from the concentric in-flow design of the polyimide inflow sleeve 15 in the flow channel 13 acts as a lossy material to absorb the microwave energy as well as to cool the feedline 20 for percutaneous use.

In another embodiment, the fluid seal 8 may also be formed from solid wire machined component or a cylindrical conductor filled with solder. The fluid seal 8 is thereafter coupled to the outer conductor 56 (joint E), as shown in FIGS. 3-4. This may be accomplished by soldering the fluid seal 8 to the outer conductor 56, such as by melting the solder of the fluid seal 8 and inserting the outer conductor 56 therein.

The distal portion 44 includes a conductive member 45 that may be formed from any type of conductive material, such as metals (e.g., copper, stainless steel, tin, and various alloys thereof). The distal portion 44 may have a solid structure and may be formed from solid wire (e.g., 10 AWG). In another embodiment, the distal portion 44 may be formed from a hollow sleeve of an outer conductor of coaxial cable or another cylindrical conductor. The cylindrical conductor may then be filled with solder to convert the cylinder into a solid shaft. More specifically, the solder may be heated to a temperature sufficient to liquefy the solder within the cylindrical conductor (e.g., 500° F.), thereby creating a solid shaft.

As shown in FIGS. 2 and 3, the distal portion 44 is coupled to the tip 48, which may be formed from a variety of heat-resistant materials suitable for penetrating tissue, such as metals (e.g., stainless steel) and various thermoplastic materials, such as poletherimide, polyimide thermoplastic resins, an example of which is Ultem® sold by General Electric Co. of Fairfield, Conn. The tip 48 may be machined from various stock rods to obtain a desired shape. The tip 48 may be attached to the distal portion 44 using various adhesives, such as epoxy seal. If the tip 48 is metal, the tip 48 may be soldered to the distal portion 44 or may be machined as one continuous component.

Figure 6:
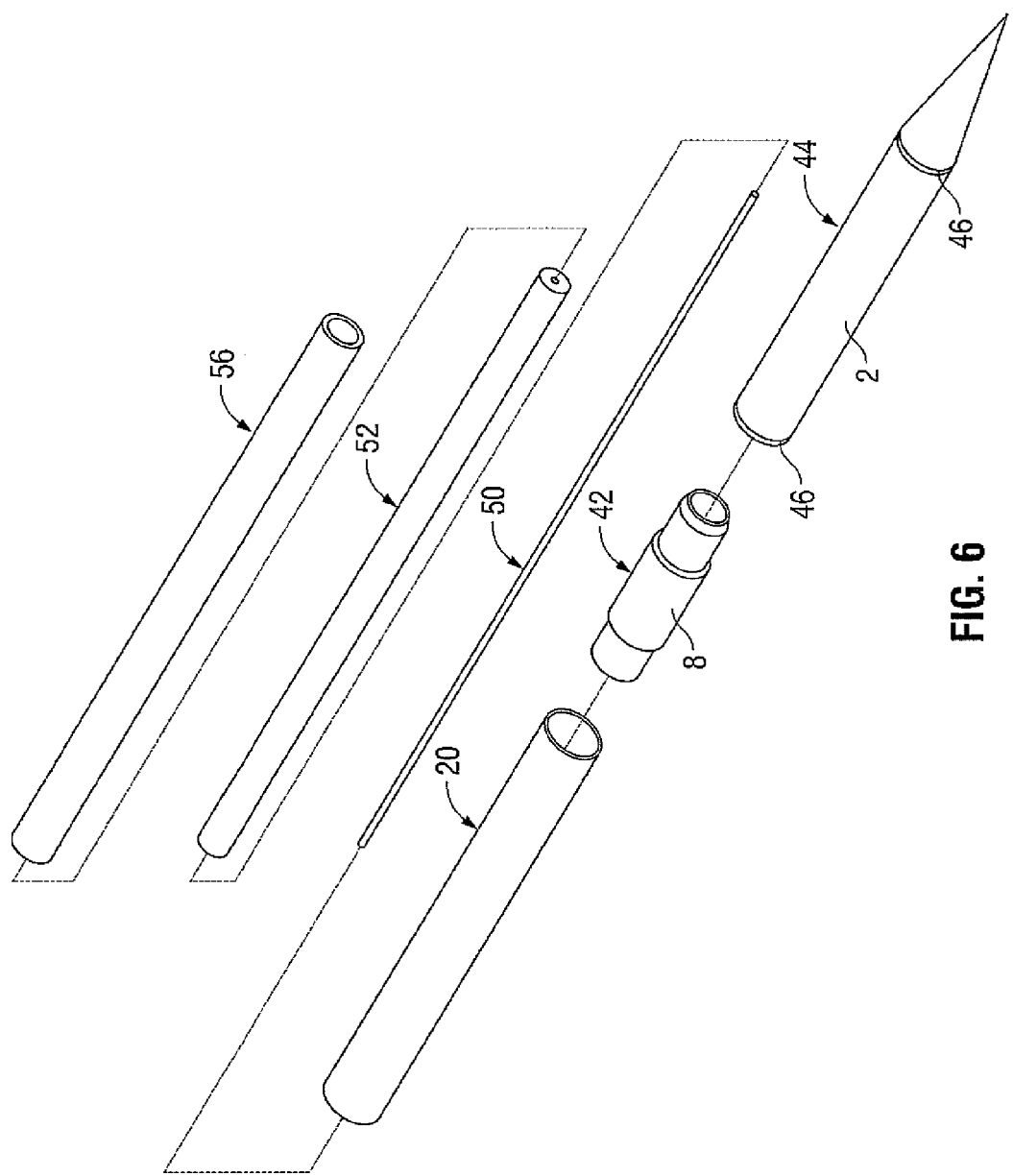
FIG. 6 is an exploded view of the microwave antenna assembly according to the present disclosure.

FIG. 6 is an exploded view of the microwave antenna assembly 12. The microwave antenna assembly 12 includes a proximal portion 42 and a distal portion 44. The proximal portion 42 may include an inner conductor 50, an inner insulator layer 52, and an outer conductor 56. The proximal portion 42 may also include a flow channel 13 defined therein (not shown) that includes an inflow channel 17a and an outflow channel 17b that are separated by a polyimide inflow tube 15. The polyimide inflow tube 15 (not shown) may be inserted into a pocket of a fluid seal 8 to cool the proximal portion 42. The distal portion 44 includes an inner conductor 50, a distal radiating section 51, an injection molded seal 46, and a ceramic layer 2.

Figure 7A:
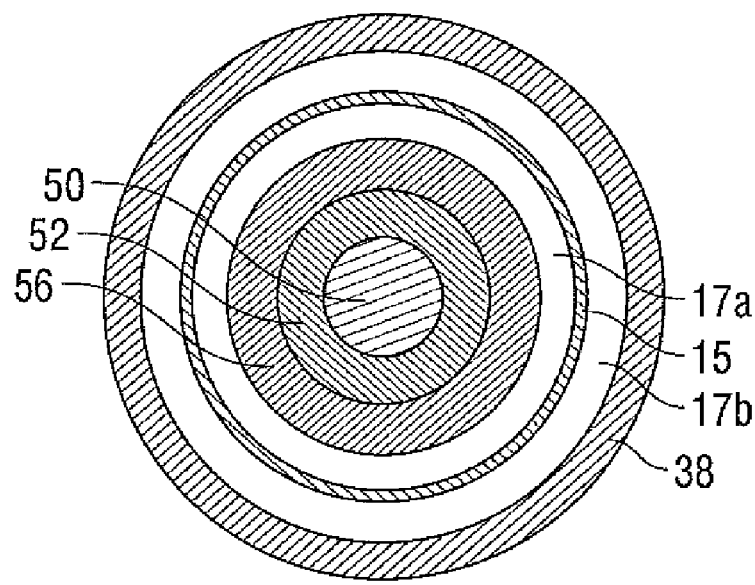
FIGS. 7A-7C are enlarged cross-sectional views of sections A-A, B-B, and C-C of the microwave antenna assembly of FIG. 4.
Figure 7B:
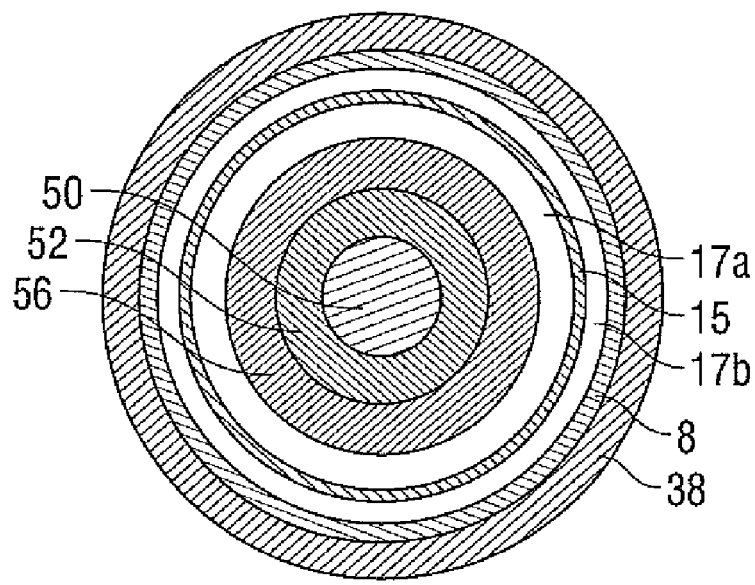
Figure 7C:
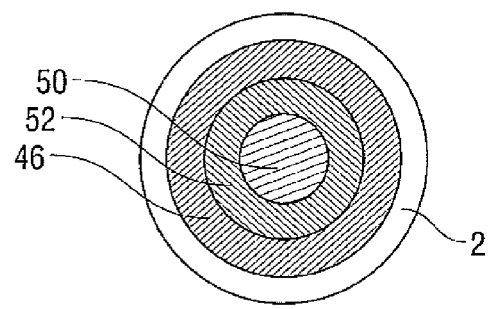

FIGS. 7A-7C are enlarged cross-sectional views of sections A-A, B-B, and C-C of the microwave antenna assembly of FIG. 4. FIG. 7A illustrates a cross section at section A-A. Section A-A illustrates from the inside towards the outer surface, an inner conductor 50, insulator 52, outer conductor 56, flow channel 13 (specifically inflow channel 17a), polyimide inflow tube 15, flow channel 13 (specifically outflow channel 17b), and coolant jacket 38.

FIG. 7B illustrates a cross section at section B-B. Section B-B illustrates from the inside towards the outer surface, an inner conductor 50, insulator 52, outer conductor 56, flow channel 13 (specifically inflow channel 17a), polyimide inflow tube 15, flow channel 13 (specifically outflow channel 17b), fluid seal 8, and coolant jacket 38. FIG. 7C illustrates a cross section taken at section C-C of the distal portion. Section C-C illustrates from the inside towards the outer surface, an inner conductor 50, insulator 52, an injection molded seal 46, and a ceramic layer 2.

Referring back to FIGS. 2-4, the microwave antenna assembly 12 may be manufactured in various steps. A coaxial cable that includes the inner conductor 50, insulator layer 52, and outer conductor 56 may be manufactured and assembled as one component. The outer conductor 56 may be soldered to the fluid seal 8, for example at joint E, to provide the electrical joint, if needed. The coolant jacket 38 may be bonded, threaded, laser welded, soldered or crimped to the fluid seal 8 at joint D. The coolant jacket 38 and the fluid seal 8 may be assembled as one component. The polyimide inflow tube 15 may be configurable to slide into a pocket of the fluid seal 8.

The inner conductor 50 is configured to slide inside a hole of the distal portion 44. The distal portion 44 is affixed to a distal end of the inner conductor 50 by laser welding, soldering or crimping at joint F. The coaxial cable, coolant jacket 38, proximal poition 42, ceramic layer 2, and distal portion 44 are placed into an injection mold cavity.

Figure 8:
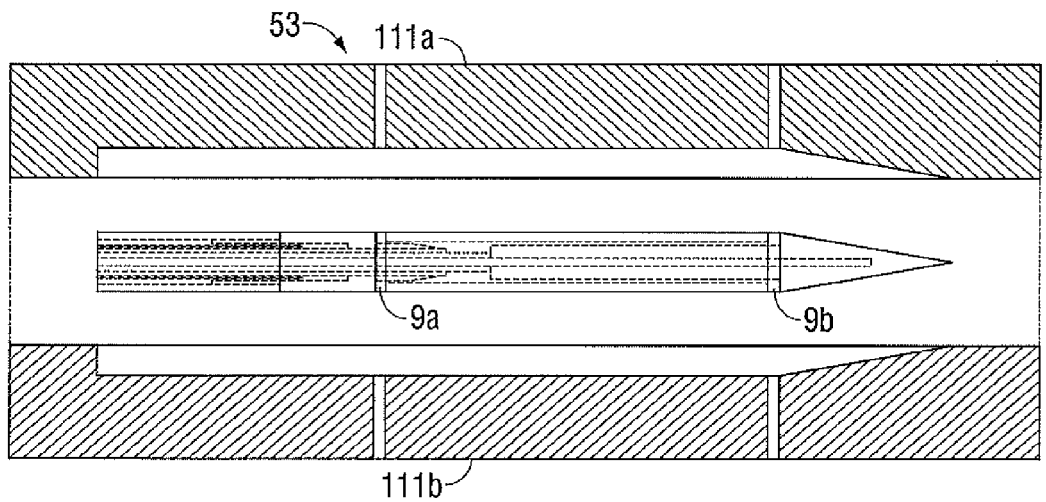
FIG. 8 is a schematic diagram of a mold according to the present disclosure.

FIG. 8 is a schematic diagram of a mold according to the present disclosure. The mold 53 is used to inject a high strength polyimide material in-between the inner conductor 50 and the ceramic layer 2. The mold 53 includes mold halves 111a and 111b. Mold halves 111a and 111b include portions/cavities to receive coaxial cable, coolant jacket 38, fluid seal 8, ceramic layer 2, and trocar tip 48. Mold halves 111a and 111b also include an inflow slot 9A and an outflow slot 9B. The mold halves 111a and 111b are clamped tightly together and heated polyimide is injected into the inflow slot 9A until the heated polyimide fills into outflow slot 9B defined therein. The polyimide flows into a cavity to form a uniform layer of polyimide layer along the distal portion 44. The polyimide material bonds the distal portion 44 and the ceramic layer to the proximal portion while providing mechanical strength to the distal portion.

Figure 9:
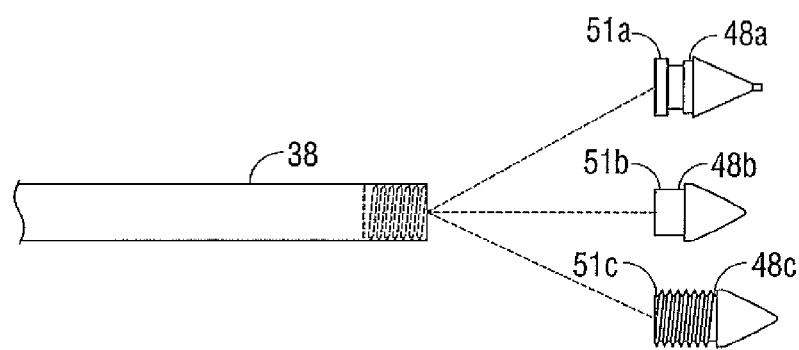
FIG. 9 is a side view of another tip of the microwave assembly of FIG. 2.

In another embodiment, the mold 53 does not include a cavity for the trocar tip 48. In such an embodiment, when the injection molding process is complete, the antenna assembly 12 is finished by installing the trocar tip 48. FIG. 9 illustrates various shapes and forms of a trocar tip 48 installed onto a sheath 38, namely a stainless steel tip 48a and a dielectric tip 48b. Both tips 48a and 48b include insertion bases 51a and 51b having an external diameter that is smaller than diameter of the tips 48a and 49 allowing for easier insertion into a sheath 38. The configuration also provides for a better seal between the tip 48 and the sheath 38. In another embodiment, the sheath 38 and tip 48c maybe threaded so as to attach to each other. Therefore, the tip 48c may be tightly screwed into the sheath 38.

The described embodiments of the present disclosure are intended to be illustrative rather than restrictive, and are not intended to represent every embodiment of the present disclosure. Various modifications and variations can be made without departing from the spirit or scope of the disclosure as set forth in the following claims both literally and in equivalents recognized in law.

What is claimed is:

1. A method of fabricating an antenna assembly, comprising the steps of:
   providing a proximal portion having an inner conductor and an outer conductor, the inner conductor extending at least partially therein;
   providing a distal portion disposed distally of the proximal portion, with the inner conductor extending at least partially therein;
   injecting a high strength material from an inflow slot to an outflow slot defined in the distal portion such that the high strength material is disposed in-between the inner conductor and a ceramic layer; and
   allowing the high strength material to bond the distal portion and the ceramic layer to the proximal portion while providing mechanical strength to the distal portion.

2. The method of fabricating an antenna in accordance with claim 1, wherein the high strength material is a polyimide material.

3. The method of fabricating an antenna in accordance with claim 1, further comprising the step of soldering a fluid seal to the outer conductor at a distal end of the proximal radiating section.

4. The method of fabricating an antenna in accordance with claim 3, further comprising the step of joining a coolant jacket to the fluid seal.

5. The method of fabricating an antenna in accordance with claim 4, wherein the coolant jacket is formed from a medical grade metal.

6. The method of fabricating an antenna in accordance with claim 4, wherein the step of joining the coolant jacket to the fluid seal is performed by at least one of laser welding, soldering, and crimping.

7. The method of fabricating an antenna in accordance with claim 3, wherein the fluid seal includes a pocket defined therein and the method further comprises inserting a polyimide inflow tube into the pocket of the fluid seal.

8. The method of fabricating an antenna in accordance with claim 1, wherein the distal portion is affixed to a distal end of the inner conductor by at least one of laser welding, soldering, and crimping.

9. The method of fabricating an antenna in accordance with claim 1, further comprising the step of joining a trocar adapted to receive a distal end of the inner conductor.

10. The method of fabricating an antenna in accordance with claim 9, wherein the step of joining the trocar is performed by at least one of welding, soldering, crimping, and threading.

11. The method of fabricating an antenna in accordance with claim 1, wherein the step of injecting the high strength material from the inflow slot to the outflow slot of the distal portion provides a uniform layer of the high strength material along the distal portion.

12. The method of fabricating an antenna in accordance with claim 1, wherein the antenna operates at 9 15 MHz, 2.45 GHz or 5.1 GHz.

13. The method of fabricating an antenna in accordance with claim 1, further comprising the step of providing an inner insulator layer disposed between the inner conductor and the outer conductor.

14. The method of fabricating an antenna in accordance with claim 13, wherein the inner insulator layer is selected from the group consisting of a tetrafluorethylene and a perfluorpropylene.

15. The method of fabricating an antenna in accordance with claim 13, wherein the inner insulator layer has a dielectric constant ranging from about 1 to about 10.

16. The method of fabricating an antenna in accordance with claim 1, further comprising the step of providing a connection hub including cable connector coupled to a coaxial cable and an inlet fluid port and an outlet fluid port defined therein, the coaxial cable includes an insulator layer separating a portion of the inner conductor and a portion of the outer conductor.

17. The method of fabricating an antenna in accordance with claim 16, wherein the connection hub further includes:
at least one inflow tube coupled to the inlet fluid port and disposed within a chamber for supplying a dielectric coolant fluid thereto; and
at least one outflow tube coupled to the outlet fluid port and in fluid communication with the inlet fluid port for withdrawing the dielectric coolant fluid therefrom.

* * * * *